United States Patent [19]
Berkhoff et al.

[11] 4,382,078
[45] May 3, 1983

[54] NOVEL WATER-BASED, DIMETHYL ETHER-PROPELLED AEROSOL COMPOSITION

[75] Inventors: Hendrik J. Berkhoff, Epe; Rudolf Zagt, Woudenberg, both of Netherlands

[73] Assignee: Polak's Frutal Works B.V., Amersfoort, Netherlands

[21] Appl. No.: 228,030

[22] Filed: Jan. 23, 1981

[30] Foreign Application Priority Data

Jan. 21, 1980 [GB] United Kingdom ................. 8001911

[51] Int. Cl.$^3$ ................................................ C09K 3/30
[52] U.S. Cl. ....................................... 424/45; 252/305; 252/522 R
[58] Field of Search .................. 252/305, 522; 424/45, 424/47

[56] References Cited

U.S. PATENT DOCUMENTS

| | | | |
|---|---|---|---|
| 3,207,386 | 9/1965 | Presant | 222/394 |
| 3,948,817 | 4/1976 | Grothoff | 252/522 |
| 4,110,428 | 8/1978 | Kuhn | 424/46 |
| 4,254,104 | 3/1981 | Suzuki | 424/170 |

FOREIGN PATENT DOCUMENTS 2036064  6/1980  United Kingdom .

*Primary Examiner*—Allan Lieberman
*Assistant Examiner*—Patricia Short
*Attorney, Agent, or Firm*—William S. Alexander

[57] ABSTRACT

Water-based aerosol compositions are disclosed which contain dimethylether as propellant and include a block co-polymer of ethylene oxide and propylene oxide as a surfactant to retain the active ingredients in the liquid phase.

5 Claims, No Drawings

NOVEL WATER-BASED, DIMETHYL ETHER-PROPELLED AEROSOL COMPOSITION

This invention relates to water-based aerosol compositions containing dimethylether (DME). Specifically, it relates to such compositions wherein dimethylether (DME) is used as the propellant and which are stabilized by a specific surfactant system.

Water-based aerosol formulations have been known for some time and have several advantages over solvent-based formulations, particularly in regard to cost and to safety, due to the flammability of most organic solvents. They also, however, are disadvantageous in some respects due to the fact that many of the items conventionally distributed via aerosols are not water soluble.

Two types of water-based aerosols have heretofore been known, namely, a three-phase system and a two-phase system. Three-phase aerosol systems are formed when using a propellant which is insoluble or substantially insoluble in the water phase. Propane/butane mixtures are an example of such water-insoluble propellants. The three phases which can be observed are the liquid water phase, the organic liquid propellant phase, and the gaseous propellant phase. These three-phase systems have certain disadvantages: almost all "active" ingredients, especially perfumes and perfume materials, show a strong preference for entering either the organic or the water phase. When not shaken properly before use, only one phase is sprayed through the dip tube, while the other phase remains in the can. Moreover, in applications such as toilet sprays, the aerosol cans are usually attached to a wall and provided with a drawstring. It is thus apparent that three-phase aerosol systems are not possible or practical in this application, because they cannot be shaken before use.

Two-phase, water-based aerosol systems consist of a homogeneous liquid phase and a gaseous phase. The liquid phase contains active ingredients, solvents, and liquefied propellant. In the case of water-based, two-phase aerosol systems, homogeneity is achieved by means of a water-soluble propellant such as DME. These types of aerosols need not be shaken before use. Unfortunately, in practice, two-phase systems are difficult to obtain, because addition of active ingredients, such as perfumes and perfume materials, to an initially homogeneous DME-water mixture causes separation. Attempts have been made to solve this problem in two ways: (1) by developing special perfumes, and (2) by addition of special solvents.

Especially designed perfumes, built up from ingredients which do not disturb the DME-water system, have been developed. Of the several hundreds of raw materials investigated, however, relatively few have turned out to be useful. This limited number of raw materials allows creation and use of perfume compositions of generally unacceptable quality.

Through addition of relatively large amounts of special solvents it has been possible to obtain a homogeneous liquid phase, but the maximum quantity of perfumes that can be incorporated in this way is approximately 0.5%. Moreover, the number of useful solvents has been found to be limited and for practical purposes restricted to acetone, lower aliphatic alcohols, and a few glycols such as mono- and dipropylene glycol, triethylene glycol, and hexylene glycol, and each of these has a disadvantage.

Addition of acetone is disadvantageous since it must be used in such high concentrations that it influences odor as well as flammability in an unacceptable way. The lower aliphatic alcohols are flammable and also liable to taxation in many countries. Addition of substantial amounts of the glycol-usually 8-12% is necessary-is disadvantageous in that it results in a fatty fallout upon spraying, which can be harmful for the surfaces on which the aerosol particles precipitate (furniture, textiles, etc.), and they can make floors slippery.

It is the object of this invention to provide two-phase, water-based aerosol compositions in which the stated problems are eliminated. It is a further object to provide such compositions wherein a greater quantity of active ingredients can be incorporated than has heretofore been found possible. Yet a further object is to provide water-based, DME-propelled aerosol compositions including, as a surfactant and stabilizer, a class of products not heretofore known to be useful in such compositions.

According to the present invention, there is provided a water-based DME-propelled aerosol composition including a block copolymer of ethylene oxide and propylene oxide having the general structural formula

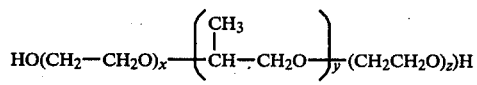

wherein $x+z$ is a whole number between about 18 and 200 and preferably between 18 and 100, $y$ is a whole number greater than 21, preferably between about 21 and 70, and the polyethylene oxide blocks constitute 20 to 80% of the total molecule by weight.

The ethylene oxide-propylene oxide block copolymer surfactant can be employed in substantially lower concentrations than are required for solvents such as the glycols cited hereinabove. The required concentration is about 1 to 6% and in most cases, between about 2 and 4%, based on the total weight of the compositions.

Aerosol compositions according to this invention have several advantages over those heretofore known in addition to their stability. One very significant advantage is the greater concentration of active ingredient, such as perfume, that can be incorporated. Whereas prior art formulations are generally capable of suspending no more than about 0.5% by weight of active ingredient, concentrations of up to about 5% can readily be suspended in the proposed compositions. Concentrations of about 0.3 to 5% are adequate for most applications.

It also appears that the use of the specified surfactants has the further advantage that the amount of DME can be substantially reduced; good results are experienced with the compositions according to the invention using 25 to 35% DME, whereas prior art formulations frequently require 40%.

The block copolymer surfactants employed in the aerosol compositions of the invention are known materials. They are commercially available in a wide range of molecular sizes and ethylene oxide/propylene oxide ratios. For identification of some specific products which can be employed, reference can be made to "CTFA Cosmetic Ingredient Dictionary", Second Edition (1977), pages 244-248, published by The Cosmetic, Toiletry and Fragrance Association, Inc., 1133 Fifteenth Street, N.W., Washington, D.C. 20005, U.S.A.

Any of the perfumes conventionally employed as odorants in these compositions can be employed such as, e.g., woody, fruity, spicy, earthy, etc. odors. Perfumes and fragrances are normally a combination of large numbers of ingredients and are employed in this manner, but are generally totally soluble in the water/DME/block copolymer carrier mixture. Other active ingredients that can be incorporated into the two-phase DME/water systems according to the invention are: insecticides, silicones, waxes, deodorizing agents, bactericides, fungicides, herbicides, resins, and corrosion inhibitors.

The general composition of the aerosol compositions according to the invention will usually be about 0.3 to 5% active ingredients, about 1 to 6% surfactant, about 15 to 35% DME, and the remainder water. Preferably, the DME content will be about 25 to 35%. Active ingredients can be any of those listed in the preceding paragraphs.

Aerosol compositions according to the invention can be prepared by the following procedure. The active ingredients, i.e., perfume, insecticide or corrosion inhibitor, are stirred into the ethylene oxide-propylene oxide copolymer until a homogeneous mixture is obtained. Water is added, with agitation, until a homogeneous mixture, either solution or emulsion, results. This mixture is changed into a conventional aerosol pressure can and the can is flushed with DME or $CO_2$ to purge air from the container. A valve is fitted to the can and clinched thereon in the conventional manner. The specified amount of DME is then added through the valve. The method of mixing the composition and charging the containers forms no part of the invention and any convenient technique other than that described can be used equally well.

The invention is illustrated by the following examples wherein parts and percentages are by weight. In Examples 1, 2, 3, 4, and 5, the surfactant is a commercially available product having a poly(oxypropylene) M.W. of about 1740 ($y=30$) and the poly(oxyethylene) units constitute about 40% ($x+y=26$) of the surfactant molecule. The composition of each of the examples remained homogeneously suspended and, when sprayed, atomized to form a fine mist without being shaken. All were adjudged to be commercially acceptable.

EXAMPLE 1

A commercial quality toilet spray aerosol composition was prepared with the following ingredients:
1.0 perfume
2.5 surfactant
66.4 water
30.0 DME

EXAMPLE 2

A room air freshener aerosol composition was prepared with the following ingredients:
3.5 perfume
5.0 surfactant
66.5 water
25.0 DME

EXAMPLE 3

An insecticide aerosol composition was prepared with the following ingredients:
0.2 Bioallethrin
0.8 piperonyl butoxide
4.0 surfactant
65.0 water
30.0 DME

EXAMPLE 4

A room freshener composition was prepared with the following ingredients:
0.3 perfume
1.0 surfactant
73.7 water
25.0 DME

EXAMPLE 5

A room freshener composition was prepared with the following ingredients:
5.0 perfume
6.0 surfactant
59.0 water
30.0 DME In addition to the surfactant specified in the foregoing examples, products of the following configurations have been successfully applied in aerosol compositions:

|     |              |          |
| --- | ------------ | -------- |
| (a) | $x + z = 38$;  | $y = 30$ |
| (b) | $x + z = 48$;  | $y = 35$ |
| (c) | $x + z = 44$;  | $y = 39$ |
| (d) | $x + z = 54$;  | $y = 39$ |
| (e) | $x + z = 42$;  | $y = 47$ |
| (f) | $x + z = 40$;  | $y = 54$ |
| (g) | $x + z = 62$;  | $y = 54$ |
| (h) | $x + z = 104$; | $y = 35$ |
| (i) | $x + z = 124$; | $y = 39$ |
| (j) | $x + z = 42$;  | $y = 67$ |
| (k) | $x + z = 196$; | $y = 67$ |

All were adjudged commercially acceptable as stabilizers of room sprays or toilet sprays.

What we claim and desire to protect by Letters Patent is:

1. A water-based, dimethyl ether-propelled aerosol composition consisting essentially of:
   (a) about 0.3 to 5% active ingredients;
   (b) about 15 to 35% dimethyl ether;
   (c) about 1 to 6% surfactant, said surfactant being a block copolymer of ethylene oxide and propylene oxide having the general structural formula

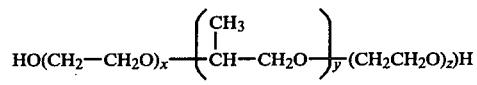

wherein $x+z$ is a whole number between about 18 and 200, y is a whole number greater than about 21, and the polyethylene oxide blocks constitute about 20 to 80% of the total molecule by weight; and
   (d) the remainder water.

2. A composition according to claim 1 wherein the active ingredient is a perfume or a perfume composition.

3. A toilet spray formulation comprising a composition according to claim 2.

4. A composition according to claim 1 wherein the active ingredient is an insecticidal agent.

5. An aerosol spray container containing an aerosol composition or system according to claim 1.